(12) United States Patent
Ramamurthy et al.

(10) Patent No.: US 8,012,420 B2
(45) Date of Patent: Sep. 6, 2011

(54) ROBUST LOW RESISTANCE VAPOR SENSOR MATERIALS

(75) Inventors: Praveen C Ramamurthy, Mansfield, OH (US); Blase S Amadio, Mansfield, OH (US)

(73) Assignee: Therm-O-Disc, Incorporated, Mansfield, OH (US)

( * ) Notice: Subject to any disclaimer, the term of this patent is extended or adjusted under 35 U.S.C. 154(b) by 1284 days.

(21) Appl. No.: 11/488,838

(22) Filed: Jul. 18, 2006

(65) Prior Publication Data

US 2008/0017507 A1    Jan. 24, 2008

(51) Int. Cl.
  *G01N 27/00* (2006.01)
  *G01N 27/04* (2006.01)
  *G01N 21/00* (2006.01)
  *G01N 27/26* (2006.01)

(52) U.S. Cl. ............... 422/82.01; 422/82.02; 422/83; 422/90; 204/400

(58) Field of Classification Search ............... None
  See application file for complete search history.

(56) References Cited

U.S. PATENT DOCUMENTS

| | | |
|---|---|---|
| 3,045,198 A | 7/1962 | Dolan et al. |
| 3,234,180 A | 2/1966 | Wu |
| 3,539,530 A | 11/1970 | Karstedt |
| 3,699,073 A | 10/1972 | Wada et al. |
| 3,848,218 A | 11/1974 | Wakabayashi et al. |
| 3,864,659 A | 2/1975 | Furuuchi et al. |
| 3,974,122 A | 8/1976 | Sato et al. |
| 4,129,030 A | 12/1978 | Dolan |
| 4,224,595 A | 9/1980 | Dolan |
| 4,329,275 A | 5/1982 | Hatanaka et al. |
| 4,592,967 A | 6/1986 | Komatsu et al. |
| 4,621,249 A | 11/1986 | Uchikawa et al. |
| 4,631,952 A | 12/1986 | Donaghey |
| 4,673,910 A | 6/1987 | Uchikawa et al. |
| 4,686,524 A | 8/1987 | White |
| 4,691,186 A | 9/1987 | Shin et al. |
| 4,752,761 A | 6/1988 | Dolan et al. |
| 4,880,857 A | 11/1989 | Mori et al. |

(Continued)

FOREIGN PATENT DOCUMENTS

AU    2004201531    10/2004

(Continued)

OTHER PUBLICATIONS

"Inco Special Products: Novamet and its Products: Nickel Oxides" [online], [retrieved on Sep. 21, 2005], retrieved from: www.incosp.com/novamet_products/nickel oxides.

(Continued)

*Primary Examiner* — Jill Warden
*Assistant Examiner* — Neil Turk
(74) *Attorney, Agent, or Firm* — Harness, Dickey & Pierce, P.L.C.

(57) ABSTRACT

Compositions for sensor films used for detecting chemical analytes within sensors, such as polymer-absorption chemiresistors (i.e., conductometric sensors) are provided. Robust sensor film compositions that have low resistance, high conductivity, and greater temperature stability and sensitivity to chemical analytes are provided, as well as methods of making these sensor films. Such sensor film compositions include a matrix having a polymer resin and a plurality of conductive particles comprising an axial-geometry conductive particle. Exemplary axial-geometry conductive particles comprise graphene, such as a carbon nanotube. Blends of conductive particles are also contemplated, including blends of axial-geometry conductive particles, such as carbon nanotubes, and carbon black.

18 Claims, 2 Drawing Sheets

U.S. PATENT DOCUMENTS

| | | | |
|---|---|---|---|
| 4,921,976 A | 5/1990 | Kabeta | |
| 4,938,860 A | 7/1990 | Wogoman | |
| 5,150,603 A | 9/1992 | Boenning et al. | |
| 5,169,909 A | 12/1992 | Okawa | |
| 5,256,574 A | 10/1993 | Neuburger et al. | |
| 5,283,308 A | 2/1994 | Bilgrien et al. | |
| 5,370,936 A | 12/1994 | Kaiya | |
| 5,512,882 A | 4/1996 | Stetter et al. | |
| 5,571,401 A | 11/1996 | Lewis et al. | |
| 5,610,324 A | 3/1997 | Lawson | |
| 5,621,038 A | 4/1997 | Chen et al. | |
| 5,686,523 A | 11/1997 | Chen et al. | |
| 5,788,833 A | 8/1998 | Lewis et al. | |
| 5,837,164 A | 11/1998 | Zhao | |
| 5,862,030 A | 1/1999 | Watkins, Jr. et al. | |
| 5,891,398 A | 4/1999 | Lewis et al. | |
| 5,911,872 A | 6/1999 | Lewis et al. | |
| 5,951,846 A | 9/1999 | Lewis et al. | |
| 5,959,191 A | 9/1999 | Lewis et al. | |
| 5,976,466 A | 11/1999 | Ratner et al. | |
| 5,979,227 A | 11/1999 | Lawson et al. | |
| 5,985,182 A | 11/1999 | Zhao | |
| 6,013,201 A | 1/2000 | Hayashida et al. | |
| 6,042,788 A | 3/2000 | De Wit et al. | |
| 6,074,576 A | 6/2000 | Zhao et al. | |
| 6,090,313 A | 7/2000 | Zhao | |
| 6,170,318 B1 | 1/2001 | Lewis | |
| 6,183,418 B1 | 2/2001 | Kuennecke | |
| 6,217,828 B1 | 4/2001 | Bretscher et al. | |
| 6,342,295 B1 | 1/2002 | Kobayashi | |
| 6,359,098 B1 | 3/2002 | Fehn et al. | |
| 6,375,821 B1 | 4/2002 | Jerome et al. | |
| 6,417,283 B1 | 7/2002 | Ikeda et al. | |
| 6,433,694 B1 | 8/2002 | Dolan et al. | |
| 6,444,323 B1 | 9/2002 | Matsumoto et al. | |
| 6,455,319 B1 | 9/2002 | Lewis et al. | |
| 6,518,371 B1 | 2/2003 | Fink et al. | |
| 6,710,123 B1 | 3/2004 | Amin-Sanayei et al. | |
| 6,740,701 B2 * | 5/2004 | Chacko | 524/492 |
| 6,815,520 B2 | 11/2004 | Yoneda et al. | |
| 6,840,069 B2 | 1/2005 | France et al. | |
| 6,868,350 B2 | 3/2005 | Zimmermann et al. | |
| 6,894,103 B2 | 5/2005 | Materne et al. | |
| 7,138,090 B2 | 11/2006 | Blok | |
| 7,171,312 B2 | 1/2007 | Steinthal | |
| 7,211,637 B2 | 5/2007 | Blok | |
| 7,501,091 B2 | 3/2009 | Munoz et al. | |
| 7,645,422 B2 | 1/2010 | Blok et al. | |
| 2002/0161140 A1 | 10/2002 | Yoneda et al. | |
| 2003/0099574 A1 | 5/2003 | Bentsen et al. | |
| 2007/0095678 A1 * | 5/2007 | West et al. | 205/775 |
| 2008/0025876 A1 | 1/2008 | Ramamurthy | |
| 2009/0130421 A1 | 5/2009 | Ramamurthy | |

FOREIGN PATENT DOCUMENTS

| | | |
|---|---|---|
| DE | 10029347 | 1/2002 |
| EP | 0110371 | 6/1984 |
| EP | 0 363 006 A2 | 4/1990 |
| EP | 0 490 523 B1 | 6/1992 |
| EP | 0 434 396 B1 | 11/1994 |
| EP | 0 833 421 A2 | 4/1998 |
| EP | 1 088 849 A2 | 4/2001 |
| EP | 1 215 248 A2 | 6/2002 |
| EP | 1 254 924 | 11/2002 |
| EP | 1467199 | 10/2004 |
| EP | 1019715 | 1/2005 |
| EP | 1602691 | 12/2005 |
| EP | 1895293 | 3/2008 |
| JP | 02 309090 | 12/1990 |
| JP | 05 043823 | 2/1993 |
| JP | 07 258548 | 2/1993 |
| JP | 08 020725 | 1/1996 |
| JP | 08 120176 | 5/1996 |
| JP | 11 106657 | 4/1999 |
| JP | 2001 158856 | 6/2001 |
| JP | 2001 221225 | 8/2001 |
| RU | 1 582 597 A1 | 11/1995 |
| WO | WO 96/37547 | 11/1996 |
| WO | WO 99/08105 | 2/1999 |
| WO | WO 99/53300 | 10/1999 |
| WO | WO 01/50117 | 7/2001 |
| WO | WO 01/88042 A1 | 11/2001 |
| WO | WO 02/08314 | 1/2002 |
| WO | WO 02/23134 A1 | 3/2002 |
| WO | WO 02/086911 | 10/2002 |
| WO | WO 2004/107359 | 12/2004 |

OTHER PUBLICATIONS

"Inco Special Products: Novamet Specialty Products" [online], [retrieved on Sep. 21, 2005], retrieved from: www.specon.com.au/Novamet.html.

"Carbon Black: Black Pearls 2000" [online], [retrieved on Aug. 28, 2006], retrieved from www.cabot-corp.com/cws/product.nsf/PDSDOCKEY/~~~BP2000?OpenDocument.

"Conductive Black: Vulcan XC72" [online], [retrieved on Aug. 28, 2006], retrieved from www.cabot-corp.com/cws/product.nsf/PDSKEY/~~~VXC72/$file/VULCAN_XC72-English.pdf?OpenElement.

"Inco Special Products: Inco Type 210 Extra Fine Nickel Powder" [online], [retrieved on Aug. 28, 2006], retrieved from www.incosp.com/products/type_210.

"SGL Carbon Group: SIGRAFIL C—continuous tow carbon fiber" [online], [retrieved on Aug. 28, 2006] retrieved from www.sglcarbon.com/sgl_t/fibers/pdf/sigrafil_c_e.pdf.

"Sigrafil C—the carbon fiber for industrial applications" [online], [retrieved on Aug. 28, 2006], retrieved from www.sglcarbon.de/sgl_t/fibers/sigra_c.html.

"Solutions for the Rubber Industry: Carbon Black Product Information" [online], [retrieved on Aug. 28, 2006], retrieved from www.degussa-fp.com/en/publikationen/produktinformationen/gummiru.Par.0029.pFile.tmp/E_PI_Printex_XE%202.pdf.

ASM International (Brinson, ed.), Engineered Materials Handbook, vol. 3, Adhesives and Sealants, (Dec. 1990), pp. 597-600.

Chen et al., "Electrochemical Synthesis of Polypyrrole Films Over Each of Well-Aligned Carbon Nanotubes," Synthetic Metals, vol. 125 (2002), pp. 289-294.

European Search Report for EP 04076097; Dated Jul. 30, 2004.

European Search Report for EP 05011207; Dated Sep. 1, 2005.

Ganter et al., "A New Generation of Addition Curing Silicone Heat Vulcanizing Rubbers," presented at Amer. Chem. Soc. Rubber Division, Cincinnati, OH, (Oct. 17-20, 2000), Paper 132.

Grate, J., "Solubility Properties of Siloxane Polymers for Chemical Sensors," Proceedings of SPIE—The International Society for Optical Engineering, vol. 2574 (1995), pp. 71-77.

Ho et al., "Review of Chemical Sensors for In-Situ Monitoring of Volatile Contaminants," SAND2001-0643, Mar. 2001.

Kim et al., "Electrical Properties of Conductive Polymers: Pet-Nanocomposites' Fibres," AUTEX Research Journal, vol. 4, No. 1 (2004), pp. 9-13.

Lewis et al., "Hydrosilylation Catalysts Derived from Cyclodextrin Organometallic Platinum Inclusion Compounds and Their Use in Command-Cure Applications," Journal of Inorganic and Organometallic Polymers, vol. 6, No. 2 (1996), pp. 123-144.

Lewis et al., "Platinum-Group Metal Cyclodextrin Complexes and Their Use as Command-Cure Catalysts in Silicones," Journal of Inorganic and Organometallic Polymers, vol. 5, No. 4 (1995), pp. 377-390.

Lewis et al., "The Chemistry of Fumarate and Maleate Inhibitors With Platinum Hydrosilylation Catalysts," Journal of Organometallic Chemistry, vol. 521 (1996), pp. 221-227.

Lin et al., "Percolated Network of Polystyrene Surface Grafted Multi-Walled Carbon Nanotubes in Polymer Thin Films," [online], [retrieved on Jul. 25, 2006], retrieved from: www.nanotubes.com.cn/papers/F-0-11-04.

March et al., Advanced Organic Chemistry; Reaction, Mechanisms, and Structures, 5th ed., Wiley & Sons, New York (2001), pp. 365-368.

March, Advanced Organic Chemistry; Reactions, Mechanisms, and Structures, 4th ed., Wiley & Sons, New York (c.1992), pp. 275-277.

Richner et al., "Grafted, Cross-Linked Carbon Black as a Double-Layer Capacitor Electrode Material," PSI Scientific Report, vol. V (2000), pp. 76-77.

Ronot et al., "Detection of Chemical Vapours with a Specifically Coated Optical-Fibre Sensor," Sensors and Actuators B, vol. 11 (1993), pp. 375-381.

Ronot et al., "Optimization and Performance of a Specifically Coated Intrinsic Optical-Fibre Sensor for the Detection of Alkane Compounds," Sensors and Actuators A, vol. 41-42 (1994), pp. 529-534.

Ronot-Trioli et al., "Solubility Interactions between Organic Vapors and Specific Polymeric Claddings for Optical Fiber Sensor," Sensors and Materials, vol. 7, No. 6 (1995) pp. 383-393.

Saruyama et al., "Development of New Hydrosilylation Cure System with Microencapsulated Platinum Catalysts"; presented at Amer. Chem. Soc. Rubber Division, Anaheim, CA, (May 6-9, 1997), Paper 64.

Schierbaum, "Application of Organic Supramolecular and Polymeric Compounds for Chemical Sensors," Sensors and Actuators B, vol. 18-19 (1994), pp. 71-76.

Hansen, George "High aspect ratio sub-micron and nano-scale metal filaments," Society for the Advancement of Material and Process Engineering, vol. 41, No. 2, pp. 2-11, (Mar. 2005).

Lonergan, Mark C. et al., "Array-Based Vapor Sensing Using Chemically Sensitive, Carbon Black-Polymer Resistors," Chem. Mater., vol. 8, No. 9, pp. 2298-2312, (1996).

Sau, K.P. et al., "Electrical conductivity of carbon black and carbon fibre filled silicone rubber composites," Die Angewandte Makromolekulare Chemie, vol. 258, No. 1, pp. 11-17, (1998).

* cited by examiner

ROBUST LOW RESISTANCE VAPOR SENSOR MATERIALS

FIELD

The present disclosure relates to sensor films, and more particularly to sensor films that detect vapor analytes.

BACKGROUND

Detection of specific target analytes, or chemical compounds, is important for many applications, including for example, detecting whether the concentration of analytes exceeds flammability limits. Target analytes are detected by sensors operating according to different detection mechanisms, known in the art. Most sensors employ a sensing component that is physically modified in the presence of specific analytes present in the environment. Thus, a sensor typically comprises a probe that includes both the sensing component and a probe body housing (including terminals for transmitting an output). The terminals are typically coupled to a processor, also part of the sensor, which analyzes the outputs received from the sensor probe to a user interface. Such a user interface typically contains an indicating device which signals a user when concentration values of an analyte have been exceeded.

Many sensors employ a sensing component that is a sensor film. Many sensor films swell, increasing in volume, while in the presence of the analytes. Various sensors available in the art utilize the physical changes in the sensor film to determine concentration of analyte present. Such sensors may include optical sensors, such as fiber optic sensors, where a beam of light is projected through an optical fiber at a sensor film cladding, and physical changes (e.g., refractive index or color) in the film are monitored. Such changes in refractive index occur when analytes are absorbed and change the physical properties of the cladding (including volumetric changes). Other sensors include surface acoustic wave sensors (SAWS), which project ultrasonic waves through the sensor film between transducers, and likewise detect any modifications in the properties of the sensor film (primarily the mass), translating those changes to the concentration of analyte present.

Another type of sensor film is a conductometric sensor, more particularly, a polymer-absorption chemiresistor sensor. A polymer-absorption chemiresistor has a polymer film sensor exposed to a surrounding atmosphere containing target analytes (chemical compounds). An electrical charge is applied across the polymer film. The polymer absorbs target analytes and this results in a volumetric change of the film, and hence the electrical resistance of the film.

Further, conductive particles may be distributed throughout the polymer film to enhance the sensitivity to resistance changes in the material when the volume of the polymer changes. However, any sensor film that relies upon physical changes resulting from absorption of the chemical analytes (i.e., volume, mass, refractive index, and resistance) is generally also sensitive to volumetric changes dependent on temperature. Further, enhancing the sensitivity to chemical analytes is desirable. Additionally, there are many applications where only a low amount of current is available and require low resistance sensors. There is a need for a low resistance sensor film composition that enhances sensitivity to desired chemical analytes, while further increasing its stability during temperature fluctuations.

SUMMARY

In one aspect, various embodiments of the present disclosure provide a conductometric sensor film for detecting chemical analytes. In certain embodiments, a conductometric sensor film for detecting one or more chemical analytes comprises a polymer matrix comprising a crosslinked polymer and a plurality of particles comprising a conductive axial-geometry particle homogeneously distributed within the matrix. In the presence of one or more chemical analytes, the sensor film exhibits a change in resistance.

In certain embodiments, a low resistance conductometric sensor film for detecting chemical analytes comprises a polymer matrix comprising a crosslinked polymer resin comprising siloxane and a plurality of particles. The plurality of particles comprises a conductive particle species comprising graphene that is homogeneously distributed within the matrix. In the presence of one or more chemical analytes, the sensor film exhibits a base resistance that is less than or equal to about 10 Ohm.

In other embodiments, a low resistance conductometric sensor film for detecting chemical analytes comprises a polymer matrix comprising a crosslinked polymer that comprises siloxane and a plurality of particles homogeneously distributed within the matrix. The particles comprise a first species selected from carbon nanotubes, nanofibers, nanofilaments, and mixtures thereof. The particles further comprise a second species that is carbon black. The sensor film exhibits a change in resistance when in the presence of one or more chemical analytes.

Further areas of applicability of the present disclosure will become apparent from the detailed description provided hereinafter. It should be understood that the detailed description and specific examples, while indicating the various aspects of the disclosure, are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

DETAILED DESCRIPTION

The following description is merely exemplary in nature and is in no way intended to limit the disclosure, its application, or uses.

The present disclosure contemplates a sensor film having improved temperature stability and sensitivity to analytes. Further, in various embodiments, the sensor film in the sensor exhibits a relatively low resistance upon exposure to one or more chemical analytes. In accordance with various aspects of the disclosure, the sensor films have increased robustness, long-term durability and sustained performance capability.

There are various challenges associated with the development of robust sensor films that have superior sensitivity to one or more chemical analytes, while exhibiting stability to temperature fluctuations, particularly for low resistance applications. In particular, there are challenges associated with the selection of conductive particles for use in the polymer matrix forming the sensor film. Often, it is difficult to stabilize and maintain a homogeneous distribution of such conductive particles due to potential phase separation and migration within the matrix. Preferably sensors are robust and capable of withstanding mechanical shock, vibration, and thermal shock, which includes maintaining a substantially homogeneous distribution of the plurality of conductive particles for long durations of use. Further, certain otherwise desirable conductive particle species may be difficult to process and/or distribute within the matrix. It is also highly desirable to increase electrical conductivity, hence decreasing the resistance of the film, while increasing and/or maintaining the sensitivity to one or more chemical analytes.

In accordance with various embodiments, a conductive polymer matrix comprises a polymer resin and a plurality of conductive particles where one or more of the species of conductive particles has an axial geometry. In various embodiments, the axial-geometry conductive particle comprises graphene, as will be discussed in more detail below. The use of the axial-geometry conductive particles improves sensitivity to target analytes and reduces sensitivity to variations in temperature, improves conductance and hence lowers resistance of the polymer matrix film in a sensor. Further, the use of axial-geometry conductive particles in accordance with the present disclosure increases stability of the particles in the matrix, thus increasing the long-term durability and performance of the polymer film.

Figure 1:
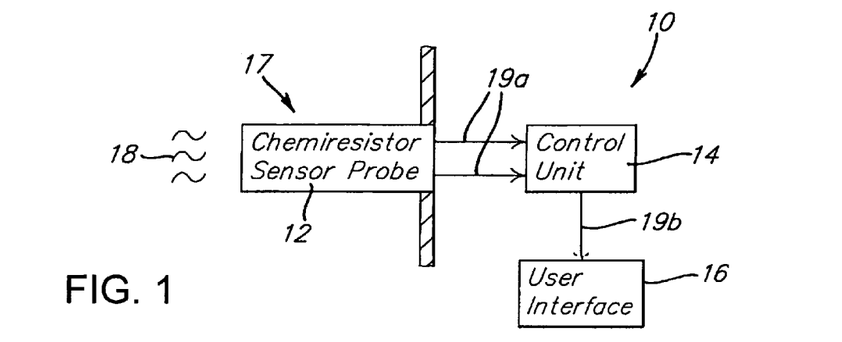
FIG. 1 is a schematic illustration of operational principles of an exemplary chemiresistor sensor.

By way of background, FIG. 1 generally depicts the major components and operational principles of an exemplary chemiresistor sensor at 10. The sensor 10 is generally comprised of a chemiresistor sensor probe 12, a control unit 14, and a user interface 16. The sensor probe 12 interacts with an external environment 17 to detect the presence of analytes, or target chemical compositions 18. The sensor probe 12 generates a raw output signal 19a based on continuous detection of analytes 18 in the external environment 17. The raw output signal 19a is processed by the control unit 14. The control unit 14 transmits a calculated output signal 19b to the user interface 16 to relay analysis of the raw output signal 19a from the sensor probe 12. The user interface 16 provides information to an external user about the sensor 10 and may range from a simple alarm signal to a complex computerized screen.

Figures 2, 3:
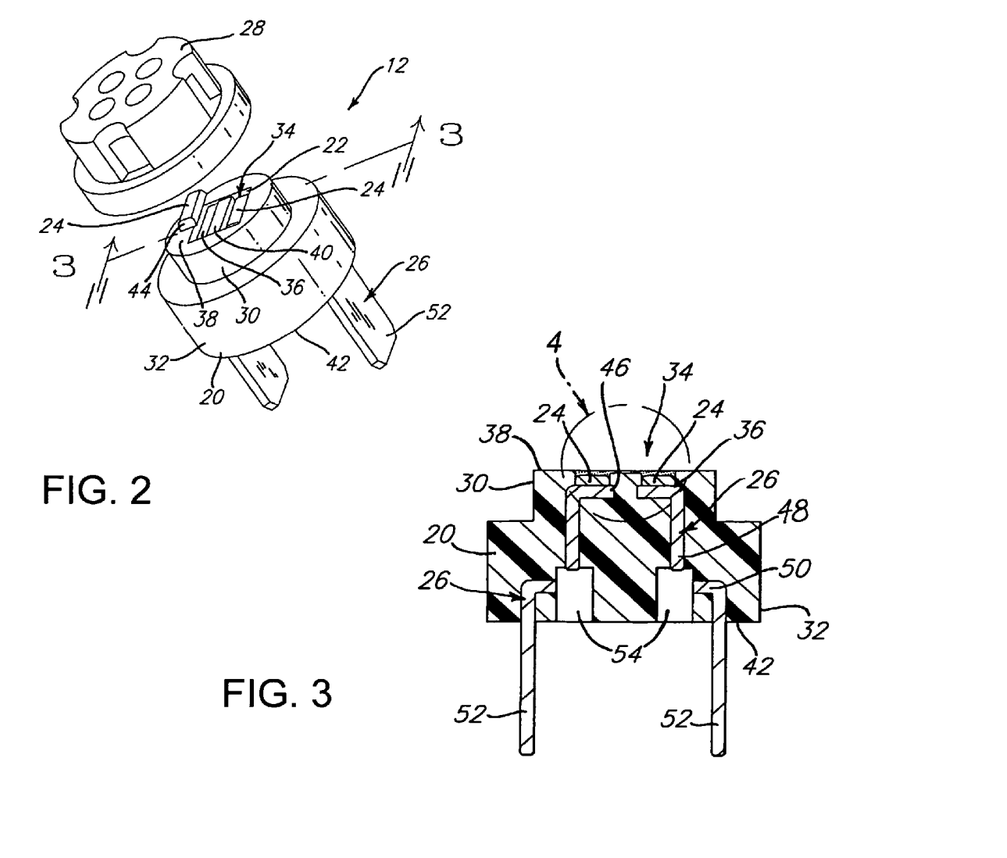
FIG. 2 is a schematic illustration of an exemplary chemiresistor sensor that can be used in accordance with the present disclosure.
FIG. 3 is a cross-sectional view taken along line 3-3 of FIG. 2.

Referring generally to FIG. 2, an example of a polymer-absorption chemiresistor sensor probe 12 compatible with the sensor film compositions of the teachings of the present disclosure is shown. The sensor probe 12 generally comprises a sensor housing 20, a conductive sensor film 22 covering a portion of the sensor housing 20 (FIGS. 2 and 3), a pair of electrodes 24 optionally disposed beneath and attached to the sensor terminals 26, and a protective cap 28. In lieu of electrodes, an alternate sensor embodiment is feasible, where the terminals 26 protrude into the sensor film 22, and serve a similar function to the electrodes 24 (i.e., deliver current through the sensor film 22).

The sensor housing 20 includes a first diameter portion 30 and a second diameter portion 32, wherein the first diameter portion is smaller in diameter than the second diameter portion. The first diameter portion 30 includes a sensing region 34. The sensing region 34 is comprised of two apertures 36 located within a first control surface 38 of the sensing region 34. Between the apertures 36 is a recessed second control surface 40 that extends across the sensing region 34. The second control surface 40 is slightly recessed below the first control surface 38.

As best shown in FIG. 3, a cross-sectional view along line 3-3 of FIG. 2, each electrode 24 sits above the apertures 36. Terminals 26 are attached to the electrodes 24 and extend through both the first diameter portion 30 and the second diameter portion 32. The terminals 26 protrude from the housing 20 at an underside 42 of the second diameter portion 32. The electrodes 24 and terminals 26 are made of a conductive material, preferably a metal. With specific reference to FIG. 4, the electrodes 24 each comprise a horizontal porous plate or mesh that is parallel to the first control surface 38 and approximately equals the width of the aperture 36. Each electrode 24 is connected to establish a conductive pathway to terminal 26. With renewed reference to FIGS. 2 and 3, a first horizontal portion 46 of the terminal 26 makes either direct or indirect contact with the portion of the sensor film 22 seated within the apertures 36 to detect changes in the resistance of the sensor film 22. Extending from the first horizontal portion 46 is a first vertical portion 48. The first vertical portion 48 extends through the first diameter portion 30 and into the second diameter portion 32 where the first vertical portion 48 transitions to an inner terminal dogleg 50 that ends in the external terminals 52 (i.e., end leads).

At the transition point between the first vertical portion 48 to the inner terminal dogleg 50, the terminals 26 each have an aperture 54. The aperture 54 receives an alignment rod (not shown) during manufacturing to permit more precise alignment of the electrodes 24 within the housing 20. The inner terminal dogleg 50 extends to the external terminals 52 which extend from the underside 42 of the second diameter portion 32. The external terminals 52 extend from the housing 20 to a suitable length to permit interconnecting the leads to a corresponding outlet (not shown) of a suitable alert device, such as an alarm.

Figure 4:
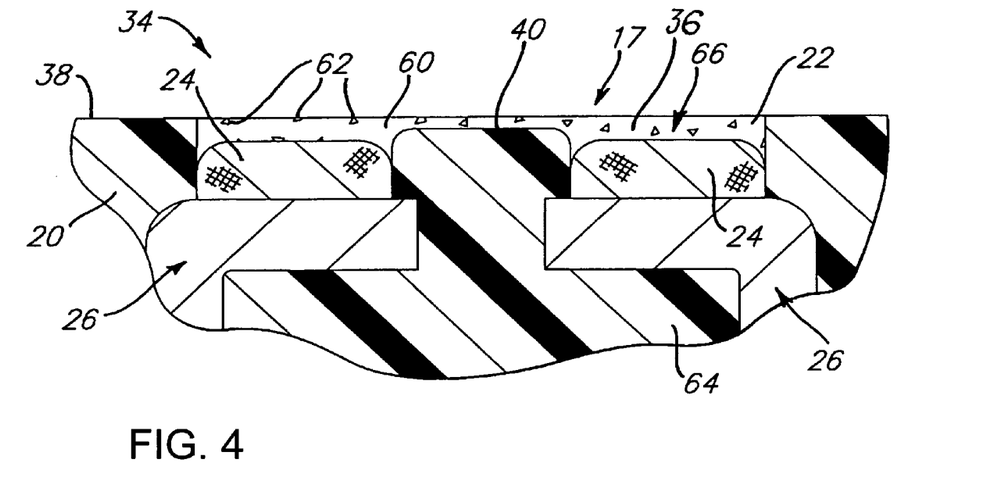
FIG. 4 is a detailed view of an exemplary sensor film region.

As best seen in FIG. 4, a detailed view of the sensing region 34 from FIGS. 2 and 3, the sensor film 22 comprises a polymer 60 with a plurality of conductive particles 62 dispersed throughout. The terminals 26 extend through a body 64 of the sensor probe housing 20 and are electrically connected to the electrodes 24. The electrodes 24 protrude into the sensing region 34 and into the sensor film 22. The electrodes 24 preferably are situated near the surface, and further across the sensor film, for even current distribution. A preferable configuration of the sensor film 22 includes conductive particles 62 distributed homogeneously (i.e., evenly) throughout the sensor film 22 body forming a conductive polymeric matrix 66. By "homogeneous" it is meant that the particles are substantially evenly distributed throughout the matrix, such that any potential detrimental effects resulting from uneven and/or localized charge distribution are minimized. "Matrix" refers generally to a polymer system having conductive filler particles distributed throughout within a polymer resin.

The conductive sensor film matrix 66 is seated upon the first control surface 38 such that the matrix 66 fills the apertures 36 and spans the center second control surface 40. The matrix 66 fills the apertures 36 so that the matrix 66 is in either direct or indirect electrical contact with both of the electrodes 24. Upon exposure of the matrix 66 to target analytes, the matrix 66 volume increases by swelling.

The polymer resin 60 of the sensor film 22 can be any polymer that readily absorbs a target analyte or chemical compound, through a gas-solid interface occurring between a surface of the sensor film 22 and the surrounding gas in the external environment 17 (FIG. 1) at a rate that is relatively proportional to the concentration of the analyte in the surrounding gas. Thus, a correlation can be made between the quantity of analyte absorbed, and the concentration of the analyte in the surrounding gas. In the exemplary sensor probe 12 depicted, the change in the volume of the sensor film 22 is correlated to the concentration of the analyte present in the gas and is further related to the resistance of the sensor film 22. Of particular interest are sensor films 22 that detect vaporous hydrocarbon compound analytes, such as one or more volatile organic compounds (VOCs). Compatible polymers for detecting VOCs include siloxane polymers. A variety of siloxane based polymers are contemplated in the present and disclosure, and further discussed below.

Figure 5:
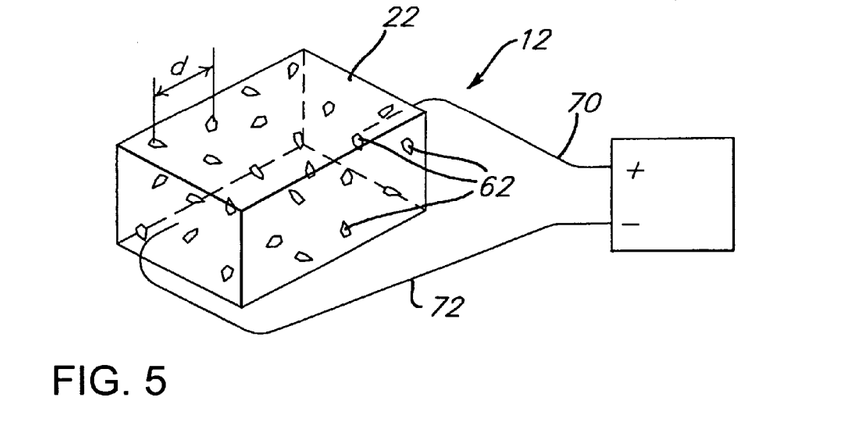
FIG. 5 is a schematic illustration of operating principles of a matrix polymer film of a polymer absorption chemiresistor.

As shown in FIG. 5, the operational principle of a polymer-absorption chemiresistor sensor probe 12 involves applying a current through the sensor film 22 between a positive 70 and a negative lead 72. Preferably, the positive and negative leads 70, 72 are terminals and/or electrodes, such as those shown at 24 and 26 in FIGS. 2-4. Conductive particles 62 are distributed throughout the sensor film 22 to enhance the electrical conductivity. Resistance measurements are taken across the sensor film 22 via monitoring of the current and potential difference across the sensor film 22 between the negative and positive leads 70, 72, and typically is measured by the processing or control unit 14 (FIG. 1) attached to the sensor probe 12. Resistance values vary with the distance "d" between the conductive particles. As this distance "d" between the conductive particles 62 increases, the resistance has a proportional relationship and thus increases. If the distance "d" decreases, the resistance also decreases. Thus, any increase or decrease in the volume of the sensor film 22 affects the overall resistance measurements.

Upon detection of a change in resistance between the positive and negative leads 70, 72, the user interface 16 (FIG. 1) provides a signal indicating the presence of the substance for which the sensor film 22 has an affinity. Consequently, the change in resistance of the sensor film 22 detected by the electrodes 70, 72 indicates the presence of the target analyte. The sensor film 22 volume may increase both by changes in temperature, as well as absorption of chemical compounds, or target analytes, into the polymer of the sensor film 22. One aspect of the present disclosure relates to minimizing effects of volume changes of the sensor film 22 due to temperature, and maximizing the absorption and sensor film 22 sensitivity to chemical compounds. Further, as appreciated by one of skill in the art, it is desirable to have a substantially homogenous distribution of the plurality of conductive particles 62 within the sensor film 22 to negate any potential localized variations that might occur.

Further, the long-term stability and maintenance of particle distribution is important to the accuracy of the device for long-term use. Potential phase separation and migration of the particles through the matrix can cause spatial variations of the conductive particles across the sensor film that can impact the capability of the sensor film to accurately measure the presence of the target analyte compounds. Long-term accuracy is a crucial parameter for sensor operation. Further, in some embodiments of the present disclosure, the sensor is suitable for use in a low-current application. An enhanced conductivity of the plurality of conductive particles can contribute to a reduction in the amount of current that must be applied, and hence improved conductivity permits certain embodiments of the present disclosure to be used as low resistance sensors in low current/low resistance applications.

By "low resistance" it is meant that the base resistance exhibited by the sensor film matrix in the absence of one or more target analytes at ambient temperature and pressure conditions is less than or equal to about 100 Ohm, more preferably less than or equal to about 50 Ohm, even more preferably less than or equal to about 40 Ohm, and most preferably less than or equal to about 20 Ohm. In some embodiments, the low resistance sensor has a base resistance of less than or equal to about 10 Ohm. For very low current applications, such as those which operate remotely with a mobile power source, for example, a battery, it is preferable that the resistance of the sensor is less than or equal to about 5 Ohm, more preferably less than or equal to about 1 Ohm, and even more preferably less than or equal to about 100 mOhm. "About" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates a possible variation of up to 5% in the value.

Further, it is preferable that sensor films have efficient and improved sensitivity to one or more target analytes, while minimizing cross-sensitivity to temperature (many chemiresistor films exhibit increased resistance upon exposure to an increase in temperature, independent of the concentration of the analyte).

Thus, in various embodiments, the disclosure provides a polymer matrix having a plurality of conductive particles. In certain embodiments, the conductive particles have an axial geometry. The term "axial geometry" refers to particles generally having a cylindrical or rod shape having an evident long or elongated axis, thus having an axial geometry. Generally, an aspect ratio (AR) for cylindrical shapes (e.g., a rod, cylinder, or fiber) is defined as $AR=L/D$ where L is the length of the longest axis and D is the diameter of the cylinder or fiber. Exemplary axial-geometry particles suitable for use in the present disclosure generally have high aspect ratios, ranging from about 500 to about 5,000, for example, where an average diameter of the axial-geometry particles ranges from less than 1 nm to about 30 nm, and the length of the axial-geometry particles can be from several hundred nanometers to greater than 10 µm. In certain embodiments of the present disclosure, the conductive particle has an axial-geometry, and includes fibers, wires, whiskers, filaments, tubes, and the like. Axial-geometry conductive particles appear to significantly enhance electrical conductivity.

In accordance with various embodiments, at least one species of the conductive particles comprises graphene. "Graphene" generally refers to a single layer of carbon arranged in a graphite structure where carbon is hexagonally arranged to form a planar condensed ring system. The stacking of graphite layers can be either hexagonal or rhombohedral, where the majority of graphite has hexagonal stacking. Carbon atoms in graphite are generally recognized as being covalently bonded with $sp^2$ hybridization. While graphite typically refers to planar sheets of carbon atoms with each atom bonded to three neighbors in a honeycomb-like structure that has a three-dimensional regular order, the term graphite does not usually include a single layer of bonded carbon due to the lack of three-dimensional bonding of carbon. Thus, as used herein, the term "graphene" comprises both single layers of elemental bonded carbon having graphite structure (including impurities), as well as graphite where carbon is bonded in three-dimensions with multiple layers. The term graphene further includes fullerene structures, which are generally recognized as compounds composed of an even number of carbon atoms, which form a cage-like fused ring polycyclic system with five and six membered rings, including exemplary $C_{60}$, $C_{70}$, and $C_{80}$ fullerenes or other closed cage structures having three-coordinate carbon atoms. Thus, in various embodiments, a graphene conductive particle is selected from the group consisting of: nanotubes, nanofibers, whiskers, rods, filaments, caged structures, buckyballs, and mixtures thereof.

In certain aspects, the conductive particles comprise a species that has both axial geometry and comprises graphene. Such species include carbon whiskers (cylindrical filaments where graphene layers are arranged in scroll-like manner with no three-dimensional stacking order) and carbon nanotubes (tubes or cylinders formed of one or more graphene layers), which exhibit excellent electrical conductivity and other physical properties. Graphene containing conductive particles tend to be inert and generally do not detrimentally react with the polymer resin or with other chemicals that they are exposed to. Further, it is believed that the geometry of nanotubes facilitates the elastic deformation or buckling of the nanotube rather than irreversible deformation or breaking, thus leading to improved robustness and long-term performance in a sensor probe. It should be noted that other suitable conductive axial-geometry particles do not necessarily include those containing carbon and can be formed of conductive metals, such as gold, copper, silver, nickel, and the like, or of boron nitride, or silicon nitride, for example.

In certain embodiments the conductive axial-geometry conductive particle comprises a carbon nanotube that comprises a graphene sheet rounded in a hollow form, which is typically recognized as having a fullerene-related structure. Carbon nanotubes have high electrical conductivity despite having a diameter as small as less than about 1 to 50 nm, in addition to high strength, as well as good chemical stability and compatibility with the polymer resin. For example, preferred carbon nanotubes according to certain embodiments of the present disclosure have a bulk electrical conductivity of about 100 S/cm or higher.

Carbon nanotubes may be a single-walled carbon nanotube species (SWNT) comprising one graphene sheet or a multi-walled carbon nanotube (MWNT) species comprising multiple layers of graphene sheet, concentrically arranged or nested within one another. A single-walled nanotube (SWNT) resembles a flat sheet that has been rolled up into a seamless cylinder. The wall thickness of the SWNT may vary, and exemplary ranges of wall thickness are from about 5 nm to about 250 nm. A multi-walled nanotube (MWNT) resembles stacked sheets that have been rolled up into seamless cylinders. In one embodiment, the MWNT may resemble 10-12 SWNTs that have been nested concentrically, one inside another. The parallel sheets are generally believed to increase electrical conductivity of the MWNT. Further, nanotubes (either SWNT or MWNT) can be processed to form clustered nanotube assemblies that are generally known as "nanoropes", which may be used in various embodiments of the present disclosure. In certain embodiments, a multi-walled carbon nanotube species has dimensions of about 10-100 nm (outer diameter) by about 5-10 nm (wall thickness) by about 0.5-50 µm (length) and a density of about 2.1 g/cc, and is commercially available from Aldrich of Milwaukee, Wis. An example of a suitable single-walled carbon nanotube is about 0.8-1.6 nm (wall thickness)×500 nm (length) with a density of about 1.7 g/cc, and is commercially available from Aldrich.

Another suitable graphene containing conductive particle is a buckminsterfullerene (i.e., a buckyball) having 60 carbon atoms, a size of about 0.4-1.6 nm, and a density of about 1.72 g/cc. It should be noted that the electrical conductivity of the buckyballs is not generally as high as axial-geometry graphene particles, such as nanotubes, and further, these conductive particles do not have an axial geometry, but are still suitable for certain sensor applications.

One benefit of the graphene conductive particles used in various embodiments of the disclosure is the improved sensitivity to one or more target analytes, as well as particularly high electrical conductivity and thus reduced resistance. Another aspect of certain embodiments is the reduction of quantity of conductive particles needed to establish the percolation threshold or the concentration of conductive particles at which the particles form a connected network for conductivity within the matrix. The percolation threshold is also empirically shown by the critical loading point for conductive particles above which a demonstrable change is observed in conductivity and/or resistance. Thus, the sensor of certain embodiments of the present disclosure that have conductive particles that are carbon nanotubes can use fewer conductive particles, while still maintaining and/or improving electrical conductivity and reducing resistance. Likewise, the lower concentration of conductive particles required to provide acceptable sensor operation, potentially reduces fabrication and material costs.

As appreciated by one of skill in the art, the matrix can comprise two or more distinct species of conductive particles to enhance sensor operation. Thus, the plurality of conductive particles may contain multiple distinct species of conductive particles, creating various blends of conductive particles. For example, two distinct conductive particles may be used, including a first species comprising carbon, preferably, graphene and a second conductive particle also comprising carbon, preferably graphene. The first and second species can optionally have an axial geometry. Alternatively, the first species may comprise graphene and the second species comprises a conductive axial-geometry particle not comprising graphene distributed in the matrix. Further, a first species of conductive particle can comprise a conductive particle comprising carbon, preferably graphene, as where a second species of conductive particle comprises a conventional conductive particle. Any number of combinations of species of conductive particles is contemplated by the present disclosure, so long as at least one of the conductive particles is a conductive particle comprising graphene.

In accordance with certain embodiments, in addition to the conductive particles comprising graphene, the matrix further comprises at least one other species of conductive particles. One particularly efficacious conductive particle is a carbon black material that has a relatively low surface area values and DBP absorption values, in essence, conductive particles that are larger in particle size and lower in aggregate size. Carbon black particles may be characterized by particle size, surface area per weight, and structure. A correlation generally exists between surface area and particle size, where a smaller particle diameter gives rise to a higher surface area. Likewise, a lower surface area value generally indicates a larger particle size diameter. Surface area is generally tested by the level of nitrogen adsorption ($N_2$) values in $m^2/g$. Testing procedures for nitrogen adsorption are outlined for example, in ASTM test D3037-91. Conductive carbon black particles for use as one species in accordance with the present disclosure preferably have a $N_2$ adsorption value (surface area per weight) of between about 8 to about 25 $m^2/g$. The most preferred ranges of $N_2$ adsorption for these carbon black species are between about 10 to about 15 $m^2/g$.

Conductive carbon black particles are characterized by structure, or the configuration, of individual particles forming an aggregate. Structure can be tested by oil dibutylphthalate (DBP) absorption in accordance with test procedure ASTM D2414, where DBP is added to 100 grams of carbon black while being mixed to generate a value of DBP ml/100 grams. A sharp increase in the torque determines the DBP value. This test indicates the structure of the particles by measuring the size of the particle aggregate. When one of the species of the plurality of conductive particles is selected to be carbon black, the DBP preferably ranges from about 1 to about 180 ml/100 g.

Carbon blacks can be formed by a variety of processing conditions, and the method of formation often relates to the physical parameters of the carbon black. Two main forms of carbon black are thermal black, formed by thermal decomposition, or cracking, of natural gas. Furnace blacks are formed in an incomplete combustion furnace process, which typically entails burning or oxidizing of a carbon rich oil-based feedstock at high temperatures. Furnace blacks generally have a small particle size, as where thermal blacks tend to have the largest particle sizes of carbon blacks. Fine thermal blacks typically have an average particle size in the range of about 100 to 200 nm, and fall into the class of carbon blacks designated N800 series. One particularly preferred fine thermal black is the class N880, which varies in average particle size, but is generally between about 90 to about 120 nm. Examples of commercially available conductive carbon black particles that fulfill the preferred physical characteristic ranges for one of species of conductive particles as described above include: Asahi 15HS or AS N880, both manufactured by Asahi Carbon Co., Ltd. of Japan; or CC N880 from Cancarb Ltd. of Alberta, Canada; and Spheron® 5000 or Spheron® 6000 both available from the Cabot Corporation of Boston, Mass. Preferred ranges of the mean particle size are from about 90 to about 400 nanometers, preferably less than 200 nm, and most preferably less than about 150 nm. One particularly preferred large particle size carbon black is the Asahi 15HS, which has an average particle size of between about 100 to about 130 nm, an $N_2$ adsorption of about 14 $m^2/g$, a DBP of about 85 ml/100 g, and a density of about 1.8 g/cc.

In certain embodiments the plurality of conductive particles additionally comprises an electrically conductive metal particle. Selection of the conductive metal particles is highly dependent on physical similarity to the other species of conductive particle present in the matrix. Examples of such electrically conductive metals include nickel, gold, silver, manganese, copper, iron, cobalt, magnesium, aluminum, mixtures and alloys thereof. Particularly preferred electrically conductive metal particles include gold, silver, and nickel.

Other exemplary suitable conductive particles that can be used with the present disclosure, as recognized by one of skill in the art, include, for example, platinum, graphite (i.e., hexagonally crystallized carbon), other carbon blacks not described above, conductive metal borides, nitrides or carbides. Further, the total amount of the plurality of conductive particles added is dependent on the individual characteristics of the particle selected, but can range from about 25 to about 75 percent by weight of the total mixture. In certain embodiments, where the conductive particle species comprises graphene, it is present at about 5 to about 20 parts per hundred resin (phr).

Distribution of the conductive particles 62 throughout the polymer base 60 can be achieved by mixing the conductive particles 62 into a polymer mixture prior to application on the sensor probe 12 to form a matrix mixture which forms the polymer base 60 of the sensor film 22. Preferably, the conductive particles 62 are homogeneously distributed throughout the polymer matrix base 60 to enhance the uniformity of resistance measurements, as discussed above. The use of the axial-geometry conductive particles 62 in chemiresistor sensor films 22, significantly enhances the sensitivity of the sensor film 22 to chemical analytes over the prior art use of conductive particles. Further, there is a significant decrease in temperature cross-sensitivity, particularly when the axial-geometry conductive particle species comprises graphene.

In various embodiments, the sensor film 22 comprises a polymer resin. In various embodiments, the polymer comprises siloxane. A "siloxane polymer" as used herein, refers to a cross-linked polymer that has a basic backbone of silicon and oxygen with side constituent groups that may be the same or different, generally described by the structural repeating unit $(-O-SiRR'-)_n$, where R and R' may be the same or different side constituent groups, and n may be any value above 2 designating the repetition of the SRU in the polymer backbone. Thus, such siloxane polymers generally comprise at least one siloxane monomer or SRU. Siloxane polymers are also known in the art as "silicone" polymers. Siloxane polymers may include polyheterosiloxanes, where side groups and/or structural repeating units may be different entities (having different side constituent groups), such as, for example, the siloxane co-polymer described by the nominal SRU formula, $(-O-SiRR')_n-(-O-S-R'''R''')_m$, wherein R and R' are distinct side groups from R'' and R'''. Further R and R' may be different from one another, likewise the same may be true for R'' and R'''. Such siloxane polymers may terminate in any variety of terminal groups, such as for example, trimethyl silyl ($(CH_3)_3Si$) terminated siloxane, or ethyl vinyl terminated siloxane.

In one embodiment of the present disclosure, the polymer of the sensor film is a cross-linked dimethylsiloxane $(-O-SiRR')_n$, where R and R' are both $CH_3$. Such side groups may be referred to as "branched" indicating side groups attached to the siloxane backbone.

In an embodiment of the present disclosure, the sensor film 22 comprises a crosslinked siloxane polymer base, wherein the siloxane polymer backbone has at least one monomer with a large hydrocarbon substituted side group represented by R' in the nominal general formula for the structural repeating unit $(-O-SiRR')_n$. A "hydrocarbon side group", as used herein, includes any hydrocarbon or hydrocarbon derived side group with two carbon atoms or greater. Examples of such hydrocarbon side groups include: alkyl and aryl groups greater than an ethyl group, branched alkyl groups, aromatics, modified hydrocarbon compounds comprising a polar groups, or mixtures thereof. Polar group modified hydrocarbons incorporate a polar molecule or molecular group into the hydrocarbon side group structure, with the effect of imparting polarity on the entire side group. Such polar atoms or groups may include, for example, oxygen, nitrogen, or ammonia, cyano or hydroxyl groups. Examples of preferred hydrocarbon side groups include without limitation: ethyl, propyl, butyl, pentyl, hexyl, heptyl, octyl, nonyl, decyl, phenyl, alkylphenyl, cyclopentyl, and phenylpropyl. Particularly preferred hydrocarbon side groups are alkyl groups with eight or more carbon atoms (octyl groups or higher). Other hydrocarbon side groups comprising a polar group include, for example, butylated aryloxypropyl, N-pyrrolidonepropyl, cyanopropyl, benzyltrimethyl ammonium chloride and hydroxyalkyl.

One example of such a siloxane having a large hydrocarbon side group includes an octyl hydrocarbon side group that forms an octylmethylsiloxane monomer. It is preferable that the siloxane polymer according to the present embodiment is crosslinked, and thus also contains a functional group capable of crosslinking during any subsequent curing or crosslinking processes. Preferred crosslinked siloxane polymers include those polymers (including homopolymers and copolymers) having at least one large hydrocarbon side substituent group. As used herein, the term "polymer" encompasses homopolymers and copolymers. The term "copolymer" generically refers to a polymeric structure that has two or more monomers polymerized with one another, and includes polymers such as terpolymers with three combined monomers. A "homopolymer" refers to a polymer formed of a single repeating monomer. One example of a preferred crosslinked siloxane having a copolymer (e.g., terpolymer) structure is poly(vinylmethylsiloxane-octylmethylsiloxane-dimethylsiloxane). Thus, the terpolymer structure has vinyl functional groups that are capable of crosslinking when exposed to crosslinking or curing agents. Ranges of the quantity of monomers in the terpolymer include (3-5% vinylmethylsiloxane)-(35-75% octylmethysiloxane)-(20%-62% dimethylsiloxane), wherein the octyl is the hydrocarbon side group, R', incorporated into the siloxane monomer, and R is a methyl side group. Another example of a preferred crosslinked siloxane having a large hydrocarbon side group according to the present disclosure is a polyphenylmethylsiloxane, where the phenyl is the large hydrocarbon side group and the polymer has vinyl terminal groups for subsequent crosslinking.

In certain embodiments, the terpolymer having a large hydrocarbon side group is further reacted with another polymer. Preferably, this additional polymer likewise comprises siloxane, and may be a homopolymer or copolymer, as described above, with functional groups capable of crosslinking. Thus, in a certain embodiment of the present disclosure, the additional copolymer comprises a polydimethyl siloxane. In another embodiment, the additional copolymer comprises a siloxane copolymer further comprising an additional large hydrocarbon side group. For example, one suitable polymer comprises (7-13% hydroxymethylsiloxane)-(87-93% octylmethylsiloxane), has an average molecular weight of about 6000, and is capable of cross-linking with the first copolymer described above.

Incorporation of large hydrocarbon side groups into monomers (which are further incorporated into polymers according to the disclosure) is achieved by polymerization performed in a conventional manner. Such a monomer, having a side group, is preferably functionalized by incorporating a reactive functional group (e.g., epoxy, amine, mercapto, methacrylate/acrylate, acetoxy, chlorine; hydride or vinyl; or hydroxyl groups) to facilitate incorporation into the siloxane backbone by polymerization, such as by conventional methods known in the art. In the case of poly(vinylmethylsiloxane-octylmethylsiloxane-dimethylsiloxane), discussed above, the octylmethylsiloxane monomer is incorporated into a copolymer with other monomers of dimethylsiloxane and vinylmethyl siloxane, where the octylmethylsiloxane monomer is preferably present in the range of from about 35% to about 75%. The octylmethylsiloxane monomer displaces the dimethylsiloxane monomer. In the case of polyphenylmethylsiloxane, substantially all of the polymer chain comprises the phenylmethylsiloxane monomer, except for the terminal ends of the siloxane polymer which are vinyl terminated (e.g., dimethylvinyl terminated siloxane). Such monomer ranges are exemplary and non-limiting and are dependent upon specific characteristics of the individual monomers employed. It is preferable to maximize the quantity of large hydrocarbon side group substituted monomers in the siloxane polymer, because maximizing the amount of large hydrocarbon side groups in a siloxane based polymer sensor film is believed to increase the overall temperature stability and analyte sensitivity.

After the large hydrocarbon side group siloxane base copolymer (or plurality of distinct copolymers) is formed (by a conventional polymerization reaction), the polymer(s) further undergo cross-linking after incorporation into the sensor film. Such crosslinking may be carried out by conventional means, such as by exposure to irradiation or peroxide, moisture cure by a condensation reaction, or a hydrosilylation reaction in the presence of a catalyst. Any method of crosslinking siloxane polymers may be used, as recognized by one of skill in the art. A preferred method of crosslinking is the hydrosilylation reaction in the presence of a catalyst, which can generally be conducted at lower temperatures and where the control over the degree of crosslinking is greater.

Crosslinking by hydrosilylation generally requires a catalyst and a crosslinking (curing) reagent which reacts with accessible functional groups on at least some of the side groups within the siloxane polymer. One example of a hydrosilylation crosslinking reaction includes, for example, polymethylhydrosiloxane octylmethylhydrosiloxane copolymer as a crosslinking reagent in the presence of a platinum catalyst to result in a crosslinked siloxane polymer. Polymethylhydrosiloxane octylmethylhydrosiloxane copolymer is commercially available as the product HAM 301, from Gelest, Inc. of Tullytown, Pa. The hydrosilylation reaction facilitates crosslinking between neighboring siloxane chains at the functional group sites. Other feasible catalyst systems that may be used for hydrosilylation (in addition to platinum) in the present disclosure include, for example: platinum carbonyl cyclovinylmethysiloxane complex used for elevated cures, such as SIP 6829 which is also commercially available from Gelest, Inc.; Rh(I) catalysts such as $(PPh_3)_3RhCl$ or $[(C_2H_4)_2RhCl]_2$, Ni catalysts, $(PPh_3)PdCl_2$, $Rh_2(OAc)_4$, $Ru_3(CO)_{12}$, and $Co_2(CO)_8$ and equivalents thereof Functional groups must be present along the siloxane backbone or at the chain ends to allow for subsequent crosslinking after polymerization. The distinct monomers within any of the copolymers may be distributed randomly or may be regularly ordered.

The crosslinking reaction is preferably achieved through a hydrosilylation reaction by adding an appropriate curing reagent and a catalyst. The rate of reaction for crosslinking is dependent on temperature and is accelerated when temperature is raised; a catalyst is added; or both. Temperature may be used to control the rate of reaction to coincide with processing needs. Further, the addition of the catalyst may be prolonged until the mixture is ready to be processed for application onto the sensor. Preferably, the curing reagent is added in the range of about 1 to about 5 weight % of the total polymer and curing reagent to form a polymer mixture. Preferably, catalyst is charged to the polymer mixture from about 0.05 to 1 weight percent of the total polymer mixture (excluding conductive particles).

A matrix mixture may be formed by admixing the plurality of conductive particles into the polymer resin (where there is more than a single species, the conductive particles are premixed prior to charging with the catalyst). The plurality of conductive particles are added in a range of from about 25 to about 75% of the total mixture depending on particle characteristics, including tendency to disperse in the matrix. It is preferred that the plurality of conductive particles is well mixed into the polymer mixture for even distribution. The polymer or matrix mixture can be blended or mixed by equipment known in the art, such as for example, a mixer (e.g., a Banbury® or Brabender® mixer), a kneader, a monoaxial or biaxial extruder (e.g., single-screw or twin-screw extruders).

The handling and flowability of a matrix mixture is dependent on the rate of crosslinking once the catalyst is added, which affects the viscosity of the mixture. The amount of time that remains for handling is generally known as the "pot life", and may range from many hours at room temperature to less than an hour if temperatures are raised to above room temperature. The crosslinking or curing reaction may be prolonged by addition of inhibitors, which are well known in the art, as a means for retarding the reaction. The crosslinking or curing reaction can be performed entirely at room temperature, or may be accelerated by heating the mixture, depending on the processing needs. Such curing temperatures range from about 30° C. to about 250° C. The mixture is then applied to the sensor surface by conventional application means (e.g., doctor blade, casting, lamination, extrusion, pad printing, spraying or silk screening). After application, further sensor components and processing may be completed, such as applying a protective cap. Curing occurs by any method known by those of skill in the art, such as by placing the sensor with a matrix mixture applied into an oven at elevated temperature, for example, for 3 to 8 hours at 120° C. to 130° C. However, many variations of curing the siloxane polymer in the matrix mixture are feasible with the present disclosure.

Details regarding the preparation of certain embodiments of the present disclosure will now be described in detail.

Example 1

A sensor film polymer matrix having a blend of conductive particles including a multi-walled carbon nanotube (MWNT) and a large particle size conductive carbon black is prepared by adding the following materials: 15.4 grams of a 3-5% vinylmethylsiloxane—35-40% octylmethylsiloxane—20-60% dimethylsiloxane terpolymer (commercially available as VAT 4326 from Gelest, Inc. of Tullytown, Pa.) which is a large hydrocarbon side group substituted siloxane polymer; 8.2 grams of a 7-13% hydromethylsiloxane—87-93% octylmethylsiloxane copolymer; 2.8 grams of multi-walled nanotubes having dimensions of 60-100 nm (outer diameter)×5-10 nm (wall thickness)×0.5-50 μm (length) available from Aldrich; 18.2 grams of Asahi 15HS (a large particle size carbon black available from Asahi Carbon Company having an $N_2$ value of 14 $m^2/g$ and a DBP of 85 ml/100 g); 0.09 grams of a platinum carbonyl cyclovinylmethylsiloxane catalyst complex (commercially available as SIP 6829 from Gelest, Inc.). The nanotubes and carbon black are pre-mixed together by hand. The particle pre-mixture is added with the other materials into a Brabender® mixer for 15 minutes at 30° C. and 80 rpm to form a matrix mixture. The mixture is then applied in a groove over electrodes in a sensor structure. The sensor structure having the matrix mixture applied is then cured for 8 hours at 130° C.

Example 2

Example 2 is prepared in a similar manner to Example 1, however the sensor film matrix has a lower concentration of multi-walled carbon nanotube particles. The following materials are added: 15.6 grams of a 3-5% vinylmethylsiloxane—35-40% octylmethylsiloxane—20-60% dimethylsiloxane terpolymer (commercially available as VAT 4326 from Gelest, Inc. of Tullytown, Pa.) which is a large hydrocarbon side group substituted siloxane polymer; 9.27 grams of a 7-13% hydromethylsiloxane—87-93% octylmethylsiloxane copolymer; 0.9 grams of multi-walled nanotubes having dimensions of 60-100 nm (outer diameter)×5-10 nm (wall thickness)×0.5-50 μm (length) available from Aldrich; 13.96 grams of Asahi 15HS (a large particle size carbon black available from Asahi Carbon Company having an $N_2$ value of 14 $m^2/g$ and a DBP of 85 ml/100 g); 0.1 grams of a platinum carbonyl cyclovinylmethylsiloxane catalyst complex (commercially available as SIP 6829 from Gelest, Inc.). The nanotubes and carbon black particles are pre-mixed by hand. Then the pre-mixture is added with other materials into a Brabender® mixer for 15 minutes at 30° C. and 80 rpm to form a matrix mixture. The mixture is then applied in a groove over electrodes in a sensor structure. The sensor structure having the matrix mixture applied is then cured for 8 hours at 130° C.

Example 3

Example 3 is prepared in a similar manner to Examples 1 and 2, however with another blend of carbon nanotubes and carbon black particles. The following materials are added: 15.5 grams of a 3-5% vinylmethylsiloxane—35-40% octylmethylsiloxane—20-60% dimethylsiloxane terpolymer (commercially available as VAT 4326 from Gelest, Inc. of Tullytown, Pa.) which is a large hydrocarbon side group substituted siloxane polymer; 9.21 grams of a 7-13% hydromethylsiloxane—87-93% octylmethylsiloxane copolymer 1.25 grams of multi-walled nanotubes having dimensions of 60-100 nm (outer diameter)×5-10 nm (wall thickness)×0.5-50 μm (length) available from Aldrich; 13.85 grams of Asahi 15HS (a large particle size carbon black available from Asahi Carbon Company having an $N_2$ value of 14 $m^2/g$ and a DBP of 85 ml/100 g); 0.1 grams of a platinum carbonyl cyclovinylmethylsiloxane catalyst complex (commercially available as SIP 6829 from Gelest, Inc.). The nanotubes and carbon particles are pre-mixed together by hand. The particle pre-mixture is then added to the other materials into a Brabender® mixer for 15 minutes at 30° C. and 80 rpm to form a matrix mixture. The mixture is then applied in a groove over electrodes in a sensor structure. The sensor structure having the matrix mixture applied is then cured for 8 hours at 130° C.

The sensor films prepared in accordance with Examples 1-3 demonstrate significant reductions in the resistance of the sensor film matrix, while also providing robustness and stability over time.

The sensor films according to the various embodiments of the disclosure provide a robust low resistance sensor, thus ensuring the accuracy of the sensor readings and durability of the matrix over time. The disclosure provides increased sensitivity to target analytes over the prior art sensor films, improving the sensor film operation. Further, the sensors have increased energy efficiency and robustness, and can be used in low current/resistance applications. The description and examples provided herein are merely exemplary in nature and, thus, variations that do not depart from the gist of the disclosure are intended to be within the scope of the disclosure. Such variations are not to be regarded as a departure from the spirit and scope of the disclosure.

What is claimed is:

1. A conductometric sensor film for detecting one or more chemical analytes comprising:
   a polymer matrix comprising a crosslinked siloxane polymer and a plurality of particles comprising a conductive axial-geometry particle species homogeneously distributed within said matrix; and
   wherein the sensor film exhibits a change in resistance when said crosslinked siloxane polymer interacts with one or more chemical analytes, wherein the sensor film is a low resistance sensor film having a base resistance of less than or equal to about 10 Ohm.

2. The sensor film according to claim 1 wherein said conductive axial-geometry particle species is selected from the group consisting of: whiskers, fibers, rods, filaments, tubes and mixtures thereof.

3. The sensor film according to claim 1 wherein said conductive axial-geometry particle species comprises carbon.

4. The sensor film according to claim 3 wherein said conductive axial-geometry particle species comprises graphene.

5. The sensor film according to claim 4 wherein at least one of said conductive axial-geometry particle species is a carbon nanotube.

6. The sensor film according to claim 5 wherein said carbon nanotube is selected from the group consisting of: single walled nanotubes, multiwalled nanotubes, and mixtures thereof.

7. The sensor film according to claim 5 wherein said carbon nanotube has a bulk electrical conductivity of greater than or equal to about 100 S/cm.

8. The sensor film according to claim 1 wherein said axial-geometry conductive particle species has an aspect ratio of greater than about 500.

9. The sensor film according to claim 1 wherein said plurality of particles further comprises a conductive carbon black particle species having an $N_2$ adsorption of between about 8 to about 25 $m^2/g$ and a DBP of about 1 to about 180 ml/100 g.

10. The sensor film according to claim 1 wherein said cross-linked siloxane polymer comprises a siloxane monomer having at least one hydrocarbon side group with greater than or equal to two carbon atoms.

11. The sensor film according to claim 1 wherein said crosslinked siloxane polymer comprises an octylmethylsiloxane monomer.

12. A conductometric sensor for detecting one or more chemical analytes comprising:
a sensor probe comprising one or more electrodes and a sensor film;
wherein the sensor film comprises a polymer matrix comprising a crosslinked siloxane polymer and a plurality of particles comprising a conductive axial-geometry particle species homogeneously distributed within said matrix;
wherein the sensor film is in electrical communication with the one or more electrodes and the sensor film exhibits a change in resistance when said crosslinked siloxane polymer interacts with one or more chemical analytes;
wherein the sensor probe generates an output signal corresponding to the change in resistance;
wherein the sensor film has a base resistance of less than or equal to about 10 Ohm.

13. The conductometric sensor according to claim 12, wherein said conductive axial-geometry particle species comprises graphene.

14. The conductometric sensor according to claim 12, wherein said conductive axial-geometry particle species is a carbon nanotube selected from the group consisting of: single walled nanotubes, multiwalled nanotubes, and mixtures thereof.

15. The conductometric sensor according to claim 14 wherein said carbon nanotube has a bulk electrical conductivity of greater than or equal to about 100 S/cm.

16. The conductometric sensor according to claim 12 wherein said plurality of particles further comprises a conductive carbon black particle species having an $N_2$ adsorption of between about 8 to about 25 $m^2/g$ and a DBP of about 1 to about 180 ml/100 g.

17. The conductometric sensor according to claim 12 wherein said cross-linked siloxane polymer comprises a siloxane monomer having at least one hydrocarbon side group with greater than or equal to two carbon atoms.

18. The conductometric sensor according to claim 12 wherein said crosslinked siloxane polymer comprises an octylmethylsiloxane monomer.

* * * * *

UNITED STATES PATENT AND TRADEMARK OFFICE
CERTIFICATE OF CORRECTION

PATENT NO.        : 8,012,420 B2
APPLICATION NO.   : 11/488838
DATED             : September 6, 2011
INVENTOR(S)       : Praveen C. Ramamurthy et al.

Page 1 of 1

It is certified that error appears in the above-identified patent and that said Letters Patent is hereby corrected as shown below:

Column 10,
Line 19, "(-O-S-R"R''')" should be --(-O-Si-R"R''')--.

Column 12,
Line 27, after "thereof", insert --.--

Column 16,
Line 6, claim 12, after "resistance;" insert --and--.

Signed and Sealed this
Twenty-ninth Day of November, 2011

David J. Kappos
*Director of the United States Patent and Trademark Office*